(12) United States Patent
Böninger et al.

(10) Patent No.: US 7,702,375 B2
(45) Date of Patent: Apr. 20, 2010

(54) MEDICAL IMAGING APPARATUS ILLUMINATED TO REDUCE PATIENT ANXIETY

(75) Inventors: Christoph Böninger, München (DE); Peter Distler, Erlangen (DE); Gerhard Helmreich, Effeltrich (DE)

(73) Assignee: Siemens Aktiengesellschaft, Munich (DE)

( * ) Notice: Subject to any disclaimer, the term of this patent is extended or adjusted under 35 U.S.C. 154(b) by 948 days.

(21) Appl. No.: 10/845,882

(22) Filed: May 14, 2004

(65) Prior Publication Data

US 2005/0004444 A1    Jan. 6, 2005

(30) Foreign Application Priority Data

May 16, 2003   (DE) ................ 103 22 140

(51) Int. Cl.
*A61B 5/00* (2006.01)

(52) U.S. Cl. ............ 600/407; 600/410; 600/425

(58) Field of Classification Search .......... 600/418, 600/407, 410, 425; 378/20, 4, 206
See application file for complete search history.

(56) References Cited

U.S. PATENT DOCUMENTS

| | | | | |
|---|---|---|---|---|
| 4,259,584 A | * | 3/1981 | Krumme | 378/15 |
| 4,629,989 A | * | 12/1986 | Riehl et al. | 324/318 |
| 4,847,736 A | * | 7/1989 | Ho | 362/122 |
| 5,134,639 A | * | 7/1992 | Vekstein et al. | 378/15 |
| 5,336,897 A | * | 8/1994 | Watanabe et al. | 250/551 |
| 5,355,885 A | * | 10/1994 | Tsuda et al. | 600/418 |
| 5,861,865 A | * | 1/1999 | Anand et al. | 345/658 |
| 6,016,038 A | * | 1/2000 | Mueller et al. | 315/291 |
| 6,035,228 A | * | 3/2000 | Yanof et al. | 600/429 |
| 6,366,796 B1 | * | 4/2002 | Yanof et al. | 600/407 |
| 6,442,230 B1 | * | 8/2002 | Wilting et al. | 378/20 |
| 6,445,186 B1 | * | 9/2002 | Damadian et al. | 324/319 |
| 6,473,486 B2 | * | 10/2002 | Hoffman | 378/19 |
| 6,494,593 B2 | * | 12/2002 | An et al. | 362/249 |
| 6,718,005 B2 | * | 4/2004 | Hamada et al. | 378/15 |
| 6,796,994 B2 | * | 9/2004 | Ignatius et al. | 607/88 |
| 6,872,179 B2 | * | 3/2005 | Kamiyama et al. | 600/437 |
| 7,113,196 B2 | * | 9/2006 | Kerr | 345/83 |
| 2003/0012018 A1 | | 1/2003 | Kluth | |
| 2004/0158145 A1 | * | 8/2004 | Ghelmansarai et al. | 600/427 |
| 2004/0181142 A1 | * | 9/2004 | Shinno et al. | 600/407 |

FOREIGN PATENT DOCUMENTS

| | | | |
|---|---|---|---|
| DE | 19639923 A1 | * | 7/1997 |
| DE | OS 196 39 923 | | 7/1997 |
| DE | 10122826 A1 | * | 6/2002 |

(Continued)

OTHER PUBLICATIONS

Patent Abstracts of Japan Publication No. 2003-052641, for Japanese Application 2001-246873.

*Primary Examiner*—Ruth S Smith
(74) *Attorney, Agent, or Firm*—Schiff Hardin LLP

(57) ABSTRACT

A medical imaging examination apparatus has a front wall with an opening to a cylindrical examination area into which a patient to be examined can be moved, and has an illumination arrangement for the illumination of the front wall over a large surface. The illumination of the front wall reduces feelings of fear on the part of a patient, and thus simplifies conducting examinations using the examination apparatus.

21 Claims, 2 Drawing Sheets

FOREIGN PATENT DOCUMENTS

| | | | |
|---|---|---|---|
| DE | 10137919 A1 * | 6/2002 | |
| DE | OS 101 22 826 | 6/2002 | |
| DE | OS 101 37 919 | 6/2002 | |
| JP | 02098003 A * | 4/1990 | |
| JP | 63249421 | 4/1990 | |
| JP | 03029638 A * | 2/1991 | |

* cited by examiner

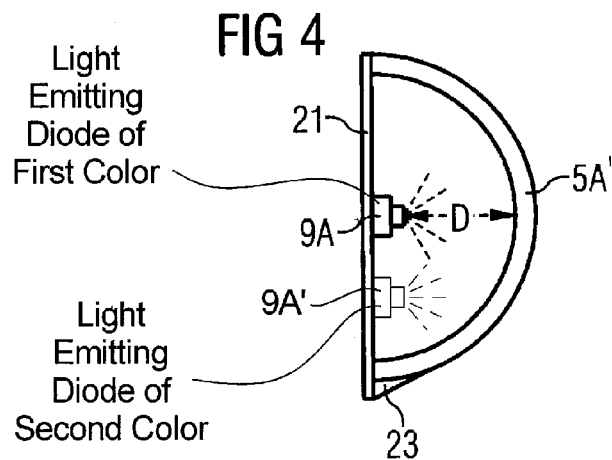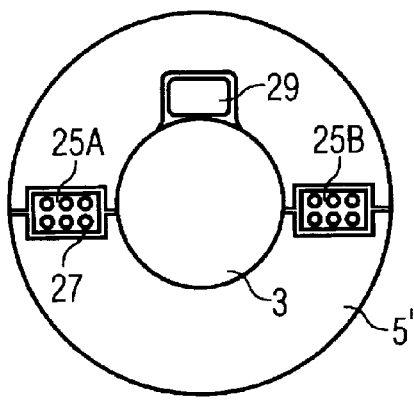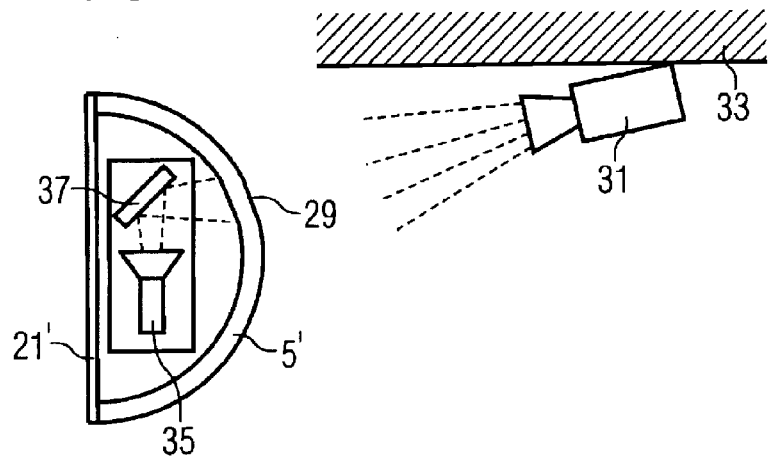

MEDICAL IMAGING APPARATUS ILLUMINATED TO REDUCE PATIENT ANXIETY

BACKGROUND OF THE INVENTION

1. Field of the Invention

The present invention concerns a medical examination apparatus for imaging of the type having a front wall with an opening to a cylindrical examination area into which a patient to be examined can be moved.

2. Description of the Prior Art

For the examination of a patient using a medical imaging apparatus, a part to be examined of the patient is brought into an examination area of the medical imaging apparatus. For example, in magnetic resonance tomography devices, computed tomography devices, and positron emission tomographs, the examination areas are usually cylindrical in shape. So that the entire patient can be brought into the examination area, the examination area has a diameter that is somewhat larger than the average shoulder width (approx. 60 cm). The examination area is surrounded by elements for imaging that are contained in a large housing, generally filling most of a room.

Upon seeing the large examination apparatus, simply the thought of being placed inside the tunnel-shaped examination area causes unpleasant feelings in most patients; when the patient is actually placed in the examination area these feelings can become stronger, to the point of claustrophobic panic attacks caused by the narrow surroundings. In other words, the sight of the examination apparatus, as well as the later placement of the patient into the examination area, together with its perceived narrowness, causes feelings of concern, anxiety or even fear in the patient.

In order to enable an examination to be carried out in spite of this fear, the patient is given a more or less strong sedative. This has the effect of limiting the patient's reactions well beyond the time required for the examination, and is often felt by the patient to be unpleasant or even damaging to the patient's health.

Translucent material is used in the illumination of, for example, advertising spaces or designer furniture. Due to its optical properties, e.g. its light conductivity due to its internal total reflection, it can be illuminated over large surfaces. An example of such a material is the polyester PET-G (polyethylene terephthalate glycol).

Light-emitting diode modules, for example the LINEARlight module made by the firm OSRAM, are used for example for light coupling in emergency beacons, in illuminated advertisements, or in path markers.

SUMMARY OF THE INVENTION

An object of the present invention is to design the appearance of a medical imaging apparatus in such a way that the patent will be pleasantly affected, and his or her feelings of fear will be reduced.

According to the present invention, this object is achieved by a medical imaging apparatus, having a front wall with an opening to a cylindrical examination area into which a patient to be examined can be moved, and having an illumination arrangement for the illumination, over a large surface, of the front wall.

A front wall illuminated over a large surface using such an illumination arrangement dominates the perceived appearance of the examination apparatus, in relation to the opening to the examination area. By an appropriate choice of the illumination arrangement, the mood of the patient can be influenced by, for example, color and brightness. This has the advantage that in many cases it becomes unnecessary to administer a sedative. The resulting improved cooperation of the patient accelerates the examination, and reduces the amount of time he or she must spend in the examination apparatus.

In one embodiment of the present invention, the front wall and the adjacent inner housing wall form a hermetically sealed component around the hollow space. This has the advantage that no foreign objects can alter the optical properties of the system. For example, foreign objects situated on the backside of the front wall would hinder the illumination effect, and thus would change the visual appearance. With the use of PET-G polyester for the front wall and for the inner housing wall, the two parts can be formed, for example, using a deep-drawing method, and can be connected to one another at their contact points, e.g. by heating. This has the advantage that the hermetically sealed hollow space is created already when the front wall is made, and can be kept free of foreign objects.

A further advantage that does not relate solely to a completely hermetically sealed hollow space is that due to the double wall system of the component, formed by the front wall and the adjacent inner housing wall, in the area of the front wall there is an acoustic decoupling of the examination apparatus from the surrounding environment. This is particularly advantageous in a magnetic resonance apparatus, because here the noise to which the patient under examination is exposed is in considerable part communicated through the front wall to the air before reaching the patient. With the aid of an additional layer of foam between the component and the magnetic resonance apparatus, a noise suppression of several tens of decibels can easily be achieved.

In a further development, the illumination arrangement is an arrangement for the emission of light and/or a control and regulation unit for controlling and regulating the intensity and/or the color of the illumination. This has the advantage that the illumination, for example by lamps or light-emitting diodes, can be monitored and can be varied dependent on the course of the examination, including the preparations. Thus, for example, when the examination room is entered a warmer, calming color tone can be selected, which can for example be reduced in intensity while the patient is being placed on a patient bed of the examination apparatus. If the head of the patient is situated in the examination area during the examination, the illumination can be adapted to the needs of the user during the examination. If the head is situated outside the examination area, the patient can also be influenced, e.g. calmed, by the illumination during the examination.

In another embodiment, the arrangement for light emission includes one or more different light-emitting diodes, fashioned for example for the emission of light of different colors. The use of different light-emitting diodes has the advantage that the illumination can be varied in many ways, and can be controlled through the use of different combinations of light-emitting diodes. If the light-emitting diodes are used with the hermetically sealed component, the hermetic seal can be maintained by arranging the light-emitting diodes in the accessible edge of the front wall.

In a further embodiment, the arrangement for emitting light and the front wall are situated in relation to another such that colored light produced by the light-emitting means is mixed at or in the front wall to form an illuminating color. This simplifies the design, because no additional elements are required for the light mixing.

In another particular specific embodiment, a number of light-emitting diodes are combined in a light-emitting diode module, and in particular a number of these diodes, arranged in an annular row, surround the opening to the examination area. This has the advantage that commercially available light-emitting diode modules can be used, which can be individually exchanged in case of failure of one or more light-emitting diodes of the light-emitting diode modules.

In another embodiment. a number of light-emitting diodes are situated between an outer edge of the front wall and the examination area. This has the advantage that a homogenous illumination of the front wall is made easier, for example by positioning the light-emitting diodes in the midpoint of a bulge in the front wall.

The arrangement for emitting light can be situated on the outer edge of the front wall. This has the advantage that it is easily accessible and can be exchanged easily in case of failure.

In another embodiment, a light-emitting diode is situated in a bored hole in the front wall, in order to couple light produced by it into the front wall. This placement of the light-emitting diode in a bored hole, which for example runs parallel to the front wall on the outer edge of the front wall, enables an efficient coupling of light into the front wall.

In a further embodiment, the front wall has, on an outer side, a deflector for deflecting light from inside the front wall outwardly. Here, the deflector can include, for example, prism-shaped recesses in the outer side of the front wall. Alternatively, or in addition, the deflector can include layers that can be fastened to the front wall, which are suitable in particular for modifying the refractive index transition from the front wall to the surrounding air. The use of a deflector for deflecting light from the interior of the front wall outwardly makes it possible to achieve a homogenous illumination of the front wall by adapting the arrangement of the light deflector to the design of the illumination arrangement.

In another embodiment, the illumination arrangement is a projector and a number of light guides that conduct light produced by the projector to the front wall and couple it into the front wall. This has the advantage that the illumination and coloring can be monitored and influenced with the aid of the projector.

In an embodiment of the examination apparatus, the front wall has a text projection area onto which text can be projected using a projection system. In particular the projection can take place onto the inner or outer side of the front wall. An advantage of this specific embodiment is that the optical characteristics of the front wall are exploited in order to make additional information easily available, for example for the operating personnel.

DESCRIPTION OF THE DRAWINGS

FIG. 4 shows a section through the front wall of the apparatus of FIG. 1, with a light-emitting diode arranged behind it.

FIG. 5 shows a front view of the front wall of a further embodiment of a medical imaging apparatus according to the invention with openings for operating elements and for a text projection area.

FIG. 6 shows two possible variants for the projection of text onto the text projection area of a further embodiment of a medical imaging apparatus according to the invention.

DESCRIPTION OF THE PREFERRED EMBODIMENTS

Figure 1:
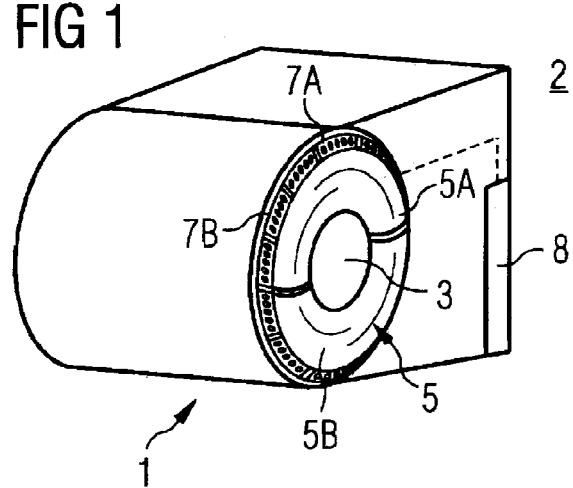
FIG. 1 shows a schematic medical imaging apparatus having an illumination arrangement in accordance with the invention.

FIG. 1 shows a hollow cylindrical scanner 1, as is often present in a medical imaging apparatus 2. For example, the hollow cylindrical scanner 1 can contain a basic magnet of a magnetic resonance tomography device, or radiation detectors of a computed tomography device or of a positron emission tomography device. The hollow cylindrical scanner 1 dominates the visual appearance of the examination apparatus 2. A patient can be introduced into opening 3, for example on a patient bed (not shown). The opening 3 is surrounded by front wall 5, which is composed of an upper front wall part 5A and a lower front wall part 5B, each manufactured from translucent material. This division simplifies the handling of the front wall 5. In cross-section, front wall 5 has the shape of a ring and, for example, is curved away from the hollow cylinder of the scanner 1 in the center radial region. On its outer edge there are situated a number of light-emitting diode modules 7A, 7B, which are connected with a control and regulation unit 8, which, for example, is integrated into a control unit of the examination apparatus 2. From the control and regulation unit 8, the light-emitting diode modules 7A, 7B are supplied with power, and individual light-emitting diodes, or all the light-emitting diodes, of the light-emitting diode modules 7A, 7B, can be driven to emit light. In particular, the control and regulation unit 8 is used to control the intensity and/or the color of the illumination.

Figure 2:
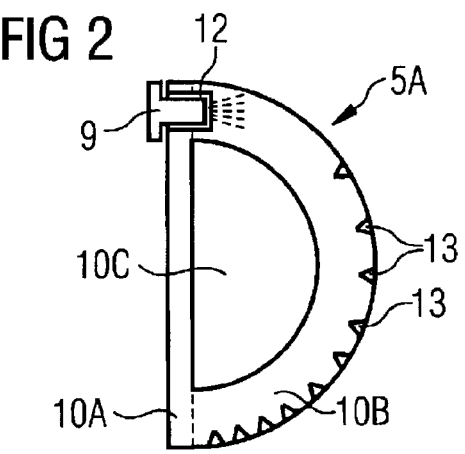
FIG. 2 shows a section through the front wall of the apparatus of FIG. 1, with a light-emitting diode integrated into the front wall.

FIG. 2 shows a section through the upper front wall part 5A of front wall 5 from FIG. 1. The front wall part 5A has been manufactured from two plates of translucent material, for example the polyester PET-G, in a deep-drawing process. One of the plates forms an adjacent inner housing wall 10A, and the other forms front wall 10B. The curvature of the front wall 10B toward the front can be seen. In the transition area of the two plates, which enclose a hermetically sealed hollow space 100, a light-emitting diode 9 is placed into a bored hole 12, and radiates light into the translucent material of front wall 10B. The front side of the front wall 10B is roughened slightly, so that a total reflection of the light propagated in the material is prevented, and light exits through the front side. The illumination effect of the front wall 10B is increased if the back wall 10A is manufactured of a translucent material that has been tinted white and the front wall 10B is manufactured of a translucent material that has been only slightly tinted green, for example as imitation glass. Due to the hermetic sealing of the front wall part 5A, the optical appearance cannot be affected by contamination in the interior. For example, the coloring is produced by the colors of the translucent material, and the colors can be accentuated by white light-emitting diodes. The desired optical impression also can be produced without active illumination. If it is desired to vary the illumination effect, it is advantageous to use a controllable active illumination arrangement, the intensity and color of which can be adjusted.

Due to the higher intensity of the coupled-in light near the light-emitting diode 9, prism-shaped recesses 13 are additionally made in the front side of front wall part 5. The recesses 13 effect an increased emission of light due to a modified angle of incidence. The distribution density of the recesses 13 increases with the distance from light-emitting diode 9, so that the intensity of the light in the translucent material, which decreases due to the coupling out and the propagation, is compensated, and a homogenous illumination of the front wall 5 is achieved.

Figure 3:
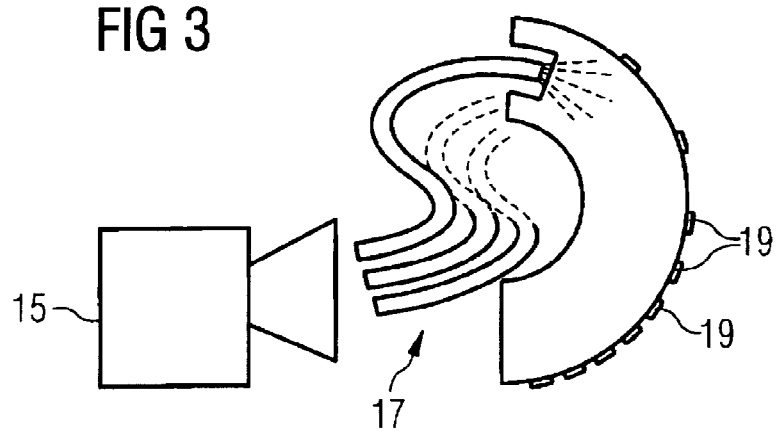
FIG. 3 shows a section through the front wall of a further embodiment of a medical imaging apparatus according to the invention. employing a projector and light guides.

FIG. 3 shows another embodiment for coupling light into the front wall part 5A. A projector 15 produces colored light that is coupled into light guides 17. Light guides 17 are routed along the outer edge of the front wall part 5A. There, the exiting light is coupled into the front wall part 5A. For the coupling in, light guides 17 can be distributed uniformly around the outer edge.

As an alternative to the prism-shaped recesses, refractive index layers 19 can be attached on the outer side of front wall part 5A, for example in the form of stickers or decals. The refractive index of refractive index layers 19 preferably lies between the refractive index of the front wall 5A and that of the surrounding air. In this way, the layers 19 prevent total reflection, and result in an increased coupling out of the light from the interior of the front wall part 5A. This effect, due to so-called "phase-shifted printing," can achieve a uniform illumination or radiation.

FIG. 4 shows an alternative design for the illumination of an upper front wall part 5A' of the front wall 5 from FIG. 1. In the direction of the hollow cylinder of the scanner 1, an adjacent inner housing wall 21 is additionally situated on which there is fastened, approximately in the center, a light-emitting diode 9A. The light-emitting diode 9A can for example be part of a light-emitting diode module that is situated annularly around the opening 3. If the curvature of the front wall part 5A' is such that the distance D from various points of the front wall part 5A' to the light-emitting diode 9A is essentially equal, this results in a uniform illumination. In the area of the opening 3, a sheathing 23 is additionally attached that produces a funnel-shaped entry for light to the opening 3, and enables easy assembly of the front wall part 5A'.

As also shown in FIG. 4, another light-emitting diode 9A' may be present, and the light-emitting diodes 9A and 9A' may be of different types, such as light-emitting diode 9A emitting light of a first color, and light-emitting diode 9A' emitting light of a second color.

FIG. 5 shows a front view of a front wall 5' with opening 3. In two operating areas situated at operating height, the front wall 5' has openings 27 into which operating units 25A, 25B can be introduced. The operating units 25A, 25B, similar to that of front wall 5', have a circuit board for the required electronic elements. Illuminated operating buttons situated in the openings 27 are set off in a particularly well-contrasted fashion from the operating units 25A, 25B, which, for example, are weakly illuminated. In addition, the front wall 5' has an opening for a text projection unit 29 on which, for example, patient data or information accompanying the examination are projected. The text projection unit 29 can be illuminated with particular colors such that a high contrast to the text is achieved. In addition, indications for the patient or for the operating personnel can be incorporated into the text projection, for example technical data concerning the position of the patient bed, the brightness of the illumination, etc.

The front wall 5' preferably is subdivided further into an upper part and a lower part, each of which is hermetically sealed.

FIG. 6 shows two possible positions of a projection system required for projection or illumination. For example, projector 31 can be fastened, at some distance from the examination apparatus, to a ceiling 33 of a room in which the examination apparatus is located. In addition to the illumination of text projection unit 29, it can also be used to illuminate the front wall 5'. Alternatively, a projection system 35 can be used having a deflecting mirror 37 that is situated in the intermediate space between the front wall 5' and the adjacent housing wall 21'.

If the front wall 5' is illuminated, for example by the projector 31, colored translucent materials can be used for front wall 5', and it can be illuminated with white light. In this case as well, a variation of the illumination intensity then results in a calming effect on the patient. Alternatively, colored light or a colored image can be projected on a front wall 5' that is for example colored white.

In the described embodiments, various types of light mixing are possible for the production of mood-influencing colors. Light having the desired color can be produced by differently colored light-emitting diodes 9 or 9A, or in a projector 15, and can be coupled into the front wall 5 directly or via light guides 17. Alternatively, the light mixing can take place in the translucent material itself, by the coupling of light of various colors into the front wall 5'.

The color of the light can be adjusted with respect to its psychological effect as well as with respect to the coloring of the surrounding premises and of the examination apparatus. In the former case, such adjustment makes it possible to induce particular moods or to neutralize feelings of fear.

In addition, alternative light effects, for example lighting patterns or transitions between different colors, can be used. For example, upon entering the examination room bright color tones such as green and white preferably are selected. Subsequently, a change preferably is made to reddish yellow-orange color tones, in order to exert a calming influence on the patient. Using remote controlling or local controlling, the light intensity or the color mixing can be subsequently controlled or adjusted in an adaptive fashion. The coloring can be adapted during the course of the examination, or can be adapted to different examinations. For example, in an examination in which the head of the examination subject is situated outside the examination area, the color can be selected to be stimulating or calming during the examination itself.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical imaging apparatus comprising:
    a scanner having an open interior volume configured to receive a patient and configured to acquire image data from the patient, said scanner having an exterior with a front wall surrounding an opening through which said open interior volume is accessed; and
    a light source located completely behind said front wall inside said exterior of said scanner, said light source emitting light that interacts with said front wall that causes a substantial surface portion of said front wall, at least surrounding said opening and being separate from said light source, to be illuminated exclusively with dispersed illumination designed to make the illuminated surface portion dominate said opening in a visual perception of said front wall at said exterior of said scanner to reduce anxiety of the patient prior to the patient being received in said open interior volume, at least a portion of said front wall being comprised of optically translucent material that conducts said light from said light source and that disperses said light, at said substantial surface portion, as said dispersed illumination.

2. A medical imaging apparatus as claimed in claim 1 wherein said scanner comprises an inner housing wall adjacent to said front wall, said front wall and said inner housing wall forming a hollow space in said scanner.

3. A medical imaging apparatus as claimed in claim 2 wherein said hollow space is hermetically sealed.

4. A medical imaging apparatus as claimed in claim 3 wherein said inner housing wall is also comprised of optically translucent material and also interacts with said light emitted by said light source to produce said dispersed illumination designed to reduce anxiety of the patient.

5. A medical imaging apparatus as claimed in claim 1 wherein said scanner forms a hollow cylinder, with said front wall forming an end face of the hollow cylinder.

6. A medical imaging apparatus as claimed in claim 1 comprising a control and regulation unit connected with said light source to control and regulate at least one of intensity and color of said illumination.

7. A medical imaging apparatus as claimed in claim 6 wherein said light source comprises at least one light emitting diode.

8. A medical imaging apparatus as claimed in claim 6 wherein said light source comprises a plurality of different types of light-emitting diodes.

9. A medical imaging apparatus as claimed in claim 8 wherein said different types of light-emitting diodes respectively emit light of different colors.

10. A medical imaging apparatus as claimed in claim 6 wherein said front wall has a peripheral edge, and wherein said light source is disposed at said peripheral edge.

11. A medical imaging apparatus as claimed in claim 10 wherein said scanner is formed as a hollow cylinder, said hollow cylinder having a cylinder wall forming said peripheral edge.

12. A medical imaging apparatus as claimed in claim 6 wherein said front wall has a bored hole therein, and wherein said light source is a light-emitting diode disposed in said bored hole for coupling light from said light-emitting diode into said front wall.

13. A medical imaging apparatus as claimed in claim 12 wherein said front wall comprises a light deflector for deflecting light outwardly from an interior of the front wall.

14. A medical imaging apparatus as claimed in claim 13 wherein said deflector comprises a plurality of prism-shaped recesses at an outer side of said front wall.

15. A medical imaging apparatus as claimed in claim 12 wherein said front wall has a refractive index, and wherein said deflector comprises at least one layer attached to said front wall having a refractive index different from the refractive index of the front wall.

16. A medical imaging apparatus as claimed in claim 6 wherein said scanner has an interior wall adjacent to said front wall, and wherein said light source comprises a light-emitting diode disposed on said interior wall that illuminates an interior side of said front wall.

17. A medical imaging apparatus as claimed in claim 6 wherein said light source emits said light at a first color, and wherein said optically translucent material has a second color, and wherein said dispersed illumination designed to reduce anxiety of the patient has a third color that is a mixture of said first color and said second color.

18. A medical imaging apparatus as claimed in claim 1 wherein said light source comprises a projector and a plurality of light guides disposed for guiding light from said projector to said front wall and to couple said light from said projector into said front wall.

19. A medical imaging apparatus as claimed in claim 18 wherein said front wall comprises a text projection area, and wherein said projector additionally generates projected text onto said text projection area.

20. A medical imaging apparatus as claimed in claim 19 wherein said front wall has an interior side, and wherein said text projection area is disposed at said interior side of said front wall.

21. A medical imaging apparatus as claimed in claim 19 wherein said text projection area is disposed at said front wall at said exterior of said scanner.

* * * * *